(12) United States Patent
Matsumoto (10) Patent No.: US 9,897,555 B2
(45) Date of Patent: Feb. 20, 2018

(54) DEFECT INSPECTION METHOD AND APPARATUS THEREFOR

(71) Applicant: HONDA MOTOR CO., LTD., Tokyo (JP)

(72) Inventor: Junichi Matsumoto, Tochigi-ken (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 15/613,428

(22) Filed: Jun. 5, 2017

(65) Prior Publication Data
US 2017/0356855 A1    Dec. 14, 2017

(30) Foreign Application Priority Data
Jun. 9, 2016 (JP) ................................ 2016-115641

(51) Int. Cl.
*G01N 21/956* (2006.01)
*G01N 21/88* (2006.01)
(Continued)

(52) U.S. Cl.
CPC .......... *G01N 21/956* (2013.01); *G01B 11/30* (2013.01); *G01N 21/8806* (2013.01);
(Continued)

(58) Field of Classification Search
CPC ... G06T 7/0002; G06T 7/0004; G06T 7/0006; G06T 7/0008; G06T 7/001; G01B 11/24; G01B 11/25; G01B 11/2513; G01B 11/2518; G01B 11/2531; G01B 11/2536;
G01B 11/254; G01B 11/30; G01B 11/303; G01B 11/306; G01N 21/88; G01N 21/8803; G01N 21/8806; G01N 21/8851;
(Continued)

(56) References Cited

U.S. PATENT DOCUMENTS 7,221,443 B2 * 5/2007 Akiyama ........... G01N 21/8806
348/E7.085
7,227,648 B2 * 6/2007 Weinhold ............... G01B 11/25
250/208.1
(Continued)

FOREIGN PATENT DOCUMENTS

| JP | 10-318938 | 12/1998 |
|---|---|---|
| JP | 2000-111490 | 4/2000 |
| JP | 2004-226316 | 8/2004 |

OTHER PUBLICATIONS

Japanese Office Action dated Dec. 12, 2017, English abstract included, 4 pages.

*Primary Examiner* — Gordon J Stock, Jr.
(74) *Attorney, Agent, or Firm* — Rankin, Hill & Clark LLP (57) ABSTRACT

A defect inspection apparatus includes a first slit light source together with a machine base in which a through hole is formed. A second slit light source and a half mirror are provided inside the through hole. First slit light from the first slit light source is directly incident on an object to be photographed (for example, an automobile body). On the other hand, second slit light from the second slit light source proceeds in a direction perpendicular to the direction in which the first slit light proceeds, and thereafter, is refracted by the half mirror, led out from the through hole, and made incident on the object to be photographed.

8 Claims, 4 Drawing Sheets

(51) Int. Cl.
*G01N 21/892* (2006.01)
*G01N 21/95* (2006.01)
*G01B 11/30* (2006.01)
*G06T 7/00* (2017.01)
*G01N 21/84* (2006.01)

(52) U.S. Cl.
CPC ....... *G01N 21/8851* (2013.01); *G01N 21/892* (2013.01); *G01N 21/95* (2013.01); *G06T 7/0004* (2013.01); *G01N 21/8921* (2013.01); *G01N 2021/8427* (2013.01); *G01N 2021/8829* (2013.01); *G01N 2021/8924* (2013.01); *G01N 2021/8925* (2013.01)

(58) Field of Classification Search
CPC ............... G01N 21/89; G01N 21/8901; G01N 21/8914; G01N 21/892; G01N 21/894; G01N 21/896; G01N 21/898; G01N 21/90; G01N 21/9036; G01N 21/94; G01N 21/95; G01N 21/9501; G01N 21/9506; G01N 21/9508; G01N 21/951; G01N 21/8921; G01N 21/8922; G01N 21/9515; G01N 21/952; G01N 21/956; G01N 21/95684; G01N 21/958; G01N 2021/8816; G01N 2021/8829; G01N 2021/8832; G01N 2021/8835; G01N 2021/8887; G01N 2021/8905; G01N 2021/8908; G01N 2021/8918; G01N 2021/8924; G01N 2021/8925; G01N 2021/8928; G01N 21/84; G01N 21/8422; G01N 2021/8411; G01N 2021/8416; G01N 2021/8427; G01N 2021/8433; G01N 2021/8438; G01N 2021/8372; G01N 2021/945
USPC .............. 382/141–152; 348/86–93, 125–133; 356/237.1–241.6, 600, 601, 604, 605, 606
See application file for complete search history.

(56) References Cited

U.S. PATENT DOCUMENTS

| | | | |
|---|---|---|---|
| 2001/0012107 A1* | 8/2001 | Toh | G01N 21/95684 356/601 |
| 2003/0095260 A1* | 5/2003 | Yoneda | G01N 21/8806 356/446 |
| 2013/0342677 A1* | 12/2013 | Park | G01B 11/25 348/87 |
| 2014/0232850 A1* | 8/2014 | Park | G01N 21/95684 348/92 |

* cited by examiner

DEFECT INSPECTION METHOD AND APPARATUS THEREFOR

CROSS-REFERENCE TO RELATED APPLICATION

This application is based upon and claims the benefit of priority from Japanese Patent Application No. 2016-115641 filed on Jun. 9, 2016, the contents of which are incorporated herein by reference.

BACKGROUND OF THE INVENTION

Field of the Invention

The present invention relates to a defect inspection method and an apparatus therefor, for inspecting whether or not a defect exists on an object to be photographed by irradiating the object to be photographed with striped illumination.

Description of the Related Art

In a manufacturing process for manufacturing automobile bodies, painting is performed on the automobile bodies. Consequently, a coating film is provided. In this instance, protuberances on the order of several tens of µm, or stated otherwise, painting defects may be formed in the coating film. If such painting defects are formed and remain as is, the aesthetic appearance of the automobile body is impaired. For this reason, after formation of the coating film, an inspection is performed in order to determine whether or not such painting defects are present.

As a defect inspection apparatus for performing this type of defect inspection, there may be cited devices with which the existence of a protuberance is detected, as disclosed in Japanese Laid-Open Patent Publication No. 2000-111490 and Japanese Laid-Open Patent Publication No. 2004-226316. More specifically, in Japanese Laid-Open Patent Publication No. 2000-111490, a defect inspection apparatus is disclosed in which a coaxial epi-illumination device is constructed to include a slit illumination source and a half mirror, and an irradiated location where a light and dark pattern is formed is photographed by a camera through the half mirror.

Although not specifically described in Japanese Laid-Open Patent Publication No. 2000-111490, the slit illumination source and the half mirror are accommodated in a casing (refer to FIG. 2 of Japanese Laid-Open Patent Publication No. 2000-111490). A through hole is formed in the casing. Striped illumination is refracted by the half mirror in the interior of the casing, and thereafter, the striped illumination passes through the through hole and is led out to the exterior of the casing, and furthermore, is made incident on an automobile body.

Further, the defect inspection apparatus disclosed in Japanese Laid-Open Patent Publication No. 2004-226316 includes slit illumination sources, which generate striped illumination for forming a stripe shaped light and dark pattern on an object to be photographed. Reflected light of the light and dark pattern that is irradiated on the object to be photographed passes through a through hole formed between the slit illumination sources, and is made incident on a half mirror. By the half mirror, the reflected light is refracted toward the side of a camera. Thereafter, the reflected light (refracted light) is subjected to a binarization process, and it is determined whether or not a protuberance exists.

In the above configurations, the slit light sources, the half mirrors, and the cameras are displaced together integrally under the action of a displacement device. More specifically, the location where the light and dark pattern is formed and the photographed location change continuously. Accompanying such a change, a defect inspection is carried out over the entire region of the coating film.

SUMMARY OF THE INVENTION

With such configurations in which reflected light that has passed through a through hole is photographed, a shadow of the machine base that supports the illumination source may be cast within the imaging range of the camera. In this case, the bright and dark pattern is not formed within the range of the shadow. Inevitably, at such a location, it is difficult to determine whether or not a defect exists.

A principal object of the present invention is to provide a defect inspection method in which it is possible to avoid casting of a shadow from a machine base within the imaging range of a camera.

Another object of the present invention is to provide a defect inspection method, which is capable of forming a stripe shaped light and dark pattern on an object to be photographed.

Yet another object of the present invention is to provide a defect inspection apparatus for implementing the aforementioned defect inspection method.

According to an embodiment of the present invention, a defect inspection method is provided for inspecting whether or not a defect exists on an object to be photographed, by irradiating striped illumination with respect to the object to be photographed, and based on an image obtained from the object to be photographed, comprising the steps of:

directly irradiating first striped illumination on the object to be photographed from a first striped illumination irradiating unit disposed in a machine base, together with refracting second striped illumination from a second striped illumination irradiating unit by a half mirror, and irradiating the second striped illumination on the object to be photographed through a through hole; and photographing the object to be photographed and which is irradiated with the first striped illumination and the second striped illumination by an image capturing unit through the half mirror;

wherein the irradiating and the photographing are continuously performed while the machine base, the second striped illumination irradiating unit, the half mirror, and the image capturing unit are displaced by a displacement device.

According to an embodiment of the present invention, a defect inspection apparatus is provided, which is adapted to inspect whether or not a defect exists on an object to be photographed, by irradiating striped illumination with respect to the object to be photographed, and based on an image obtained from the object to be photographed, comprising:

a machine base in which a through hole is formed, and in which there is provided a first striped illumination irradiating unit adapted to directly irradiate first striped illumination on the object to be photographed;

a second striped illumination irradiating unit adapted to irradiate second striped illumination on the object to be photographed through the through hole;

a half mirror adapted to refract the second striped illumination in a direction so that the second striped illumination proceeds toward the object to be photographed;

an image capturing unit adapted to photograph through the half mirror the object to be photographed which is irradiated with the first striped illumination and the second striped illumination; and a displacement device adapted to displace the machine base, the second striped illumination irradiating unit, the half mirror, and the image capturing unit.

More specifically, in the present invention, the first striped illumination from the first striped illumination irradiating unit is irradiated on a location of the object to be photographed that faces toward a location where the through hole is not formed, and further, the second striped illumination from the second striped illumination irradiating unit is irradiated on a location of the object to be photographed that faces toward the location where the through hole is formed. Therefore, the stripe shaped light and dark pattern is also formed on a location of the object to be photographed that faces toward the location where the through hole is formed.

In addition, the second striped illumination irradiating unit is constituted by a coaxial epi-illumination device. Therefore, it is difficult for the second striped illumination to be blocked by the machine base. Stated otherwise, it is easy to avoid the formation of a shadow on the object to be photographed.

In particular, the second striped illumination irradiating unit may be disposed in the through hole that is formed in the machine base. In this case, the second striped illumination is irradiated in such a manner as to proceed in a direction that intersects with respect to the direction in which the first striped illumination proceeds. Together therewith, the half mirror also is disposed in the through hole. Consequently, it is possible to more easily avoid the formation of a shadow on the object to be photographed.

In particular, the through hole may be of a rectangular shape, and together with the second striped illumination irradiating unit being installed on a first inner wall of the through hole, the second striped illumination may be irradiated in such a manner as to proceed toward a second inner wall that faces toward the first inner wall. In this case, the half mirror closes the through hole together with the second striped illumination irradiating unit.

Alternatively, the second striped illumination irradiating unit may be disposed in the vicinity of an upper opening of the through hole that is formed in the machine base, and together with the second striped illumination being irradiated so as to proceed in a direction that intersects with respect to the direction in which the first striped illumination proceeds, the half mirror may be disposed above the through hole, and the second striped illumination may be refracted toward the object to be photographed.

In accordance with the above features, blocking of the second striped illumination by the machine base is avoided with greater certainty. More specifically, a clear striped light and dark pattern is formed on the object to be photographed.

Images captured by the image capturing device are transmitted to an image analysis processing unit. Based on the results of a predetermined image analysis process (for example, a binarization process) carried out by the image analysis processing unit, it is determined whether or not a defect exists on the object to be photographed. In this instance, as described above, a clear striped light and dark pattern is formed on the object to be photographed. Therefore, since it is possible to perform the image analysis process with high reliability, it can be determined highly accurately whether or not a defect exists on the object to be photographed.

According to the present invention, together with the first striped illumination from the first striped illumination irradiating unit being made directly incident on the object to be photographed, the second striped illumination from the second striped illumination irradiating unit, which is constituted by a coaxial epi-illumination device, is refracted by the half mirror and made incident on the object to be photographed. Therefore, since it becomes difficult for the second striped illumination to be blocked by the machine base, it is possible to avoid the formation of a shadow on the object to be photographed. As a result, a clear striped light and dark pattern on the object to be photographed can be obtained.

Accordingly, highly accurate results can be obtained with regard to the image analysis process (for example, a binarization process) performed by the image analysis processing unit. Consequently, it can be determined highly accurately whether or not a defect exists in the object to be photographed.

The above and other objects, features, and advantages of the present invention will become more apparent from the following description when taken in conjunction with the accompanying drawings, in which preferred embodiments of the present invention are shown by way of illustrative example.

DESCRIPTION OF THE PREFERRED EMBODIMENTS

Preferred embodiments in relation to a defect inspection method according to the present invention, and a defect inspection apparatus for implementing such a method will be described in detail below with reference to the accompanying drawings.

Figure 1:
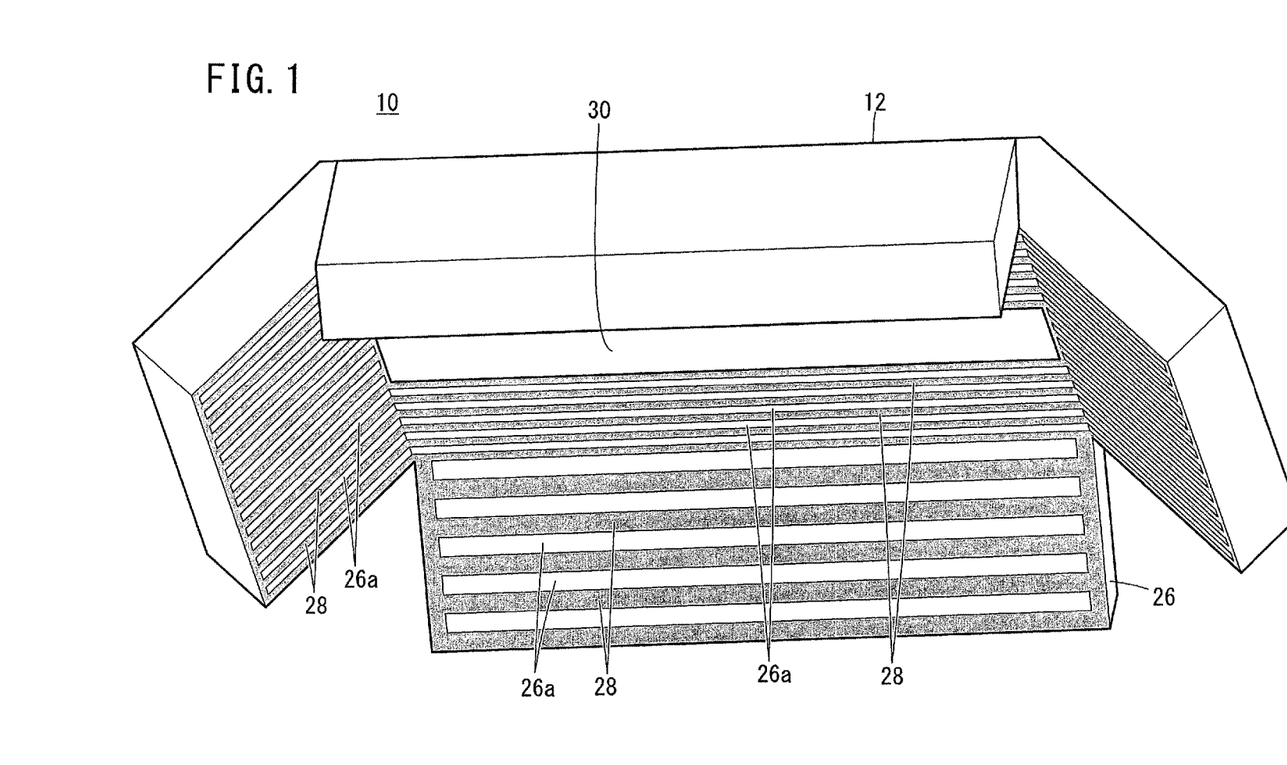
FIG. 1 is a schematic perspective view showing principal parts of a machine base that constitutes part of a defect inspection apparatus according to an embodiment of the present invention.
Figure 2:
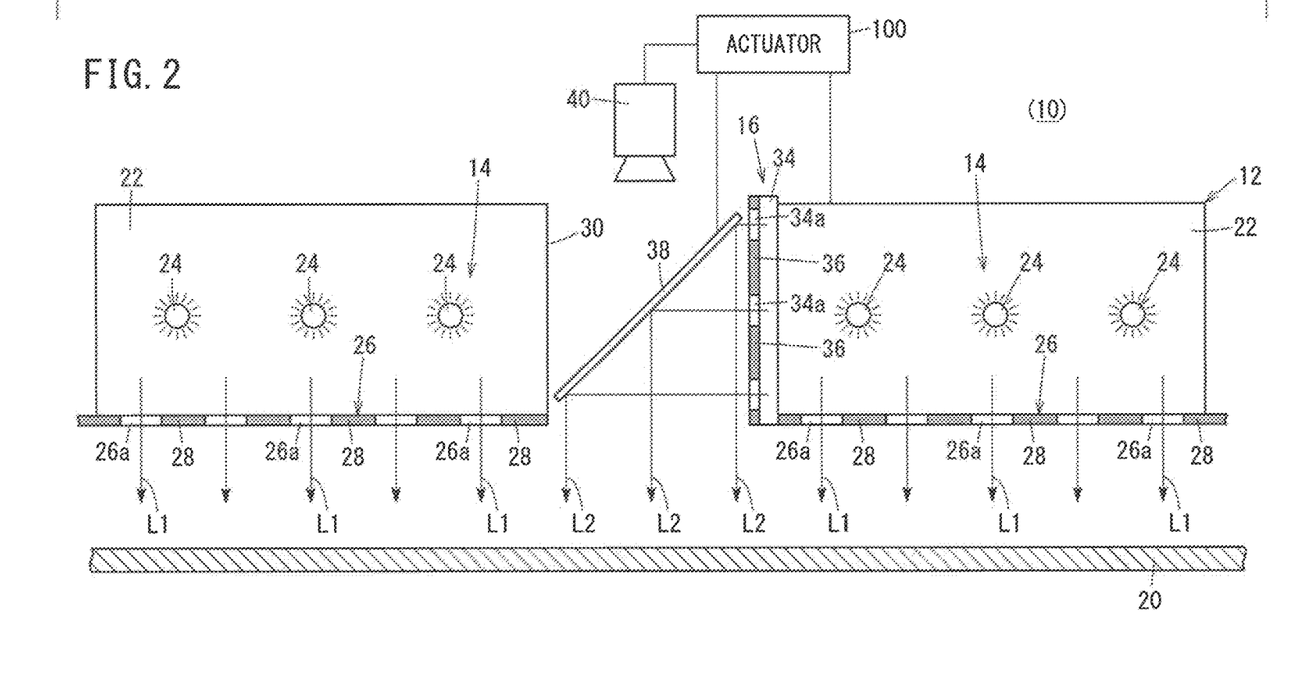
FIG. 2 is a schematic vertical cross-sectional view of principal parts of the defect inspection apparatus including the machine base shown in FIG. 1.

FIG. 1 is a schematic perspective view showing principal parts of a machine base 12 that constitutes part of a defect inspection apparatus 10 according to an embodiment of the present invention, and FIG. 2 is a schematic vertical cross-sectional view of principal parts of the defect inspection apparatus 10. The defect inspection apparatus 10 includes the machine base 12, a first slit light source 14 (first striped illumination irradiating unit), and a second slit light source 16 (second striped illumination irradiating unit) disposed on the machine base 12. First slit light L1 (first striped illumination) from the first slit light source 14 and second slit light L2 (second striped illumination) from the second slit light source 16 are both irradiated onto an automobile body 20 which is an object to be photographed.

As shown in FIG. 2, on the machine base 12, an accommodating chamber 22 is formed on a lower side facing toward the automobile body 20, and a plurality of individual white light emitting diodes (white LEDs) 24 are accommodated in the accommodating chamber 22. The first slit light source 14 is constituted by the white LEDs 24. Light emitted by the white LEDs 24 passes through translucent portions 26a of a translucent cover 26, and proceeds vertically downward toward the side of the automobile body 20 (hereinafter "translucent" means translucent or transparent).

A plurality of individual light shielding lines 28 are provided in a striped shape or pattern on the translucent cover 26. Light emitted by the white LEDs 24 is blocked at locations where the light shielding lines 28 exist. For this reason, the light that is incident on the automobile body 20 has a slit shape (striped shape). Stated otherwise, first slit light L1 is obtained.

A through hole 30 having a substantially rectangular cross section is formed substantially in the center of the machine base 12 along a thickness direction, or in other words, along a vertical direction thereof. Of course, the white LEDs 24 do not exist at the location where the through hole 30 is formed.

A cross section of the through hole 30 is of a substantially rectangular shape, and therefore, the through hole 30 has two long side walls and two short side walls as inner walls thereof. Among the inner walls, the second slit light source 16 is disposed along one of the long side walls (first inner wall).

In this instance, the second slit light source 16 includes a translucent cover 34 in which a plurality of white LEDs are accommodated, and light shielding lines 36 which are disposed on the translucent cover 34. In addition, a portion of the light emitted from the white LEDs passes through the translucent portions 34a of the translucent cover 34, and a portion of such light is blocked by the light shielding lines 36, thereby resulting in a slit shape (striped shape). Stated otherwise, second slit light L2 is obtained. Because the second slit light source 16 is disposed on a long side wall that extends in the vertical direction, the second slit light L2 proceeds in a horizontal direction that intersects with respect to the direction (a substantially vertical direction) in which the first slit light L1 proceeds, and more specifically, proceeds toward another long side wall (second inner wall) that faces toward the aforementioned long side wall.

A half mirror 38 is fixed in position in the interior of the through hole 30, at an inclined posture with respect to the vertical direction. The second slit light L2 is refracted in a vertical downward direction by the half mirror 38. The refracted second slit light L2 is led out from the through hole 30 and is made incident on the automobile body 20. As can be appreciated from this fact, the second slit light source 16 is constituted by a coaxial epi-illumination device.

A lowermost end of the inclined half mirror 38 is connected in the vicinity of a lowermost end of the other long side wall that faces toward the long side wall on which the second slit light source 16 is disposed. On the other hand, the uppermost end thereof is connected in the vicinity of an uppermost end of the second slit light source 16. Consequently, the through hole 30 is placed in a closed condition by the second slit light source 16 and the half mirror 38.

A camera 40 serving as an image capturing device is disposed above the half mirror 38. The camera 40 captures an image of a location that is visible through the half mirror 38, and more specifically, captures an image of a location irradiated with the first slit light L1 and the second slit light L2.

Images captured by the camera 40 are transmitted to a non-illustrated image analysis processing unit, for example, a computer or the like. The computer carries out an image analysis process, for example, a binarization process, and on the basis of the results of such an analysis, a determination is made as to whether or not a defect exists. Such an image analysis process and a determination method are well known, and accordingly, detailed description of such features is omitted.

In the above configuration, the machine base 12 and the camera 40 are displaced integrally by a displacement device (for example, an actuator 100 or the like). Consequently, the location irradiated with the first slit light L1 and the second slit light L2, and the location photographed by the camera 40 change continuously.

The defect inspection apparatus 10 according to the present embodiment is constructed basically in the manner described above. Next, operations and effects of the defect inspection apparatus 10 will be described in relation to a defect inspection method according to the present embodiment.

In order to determine whether or not a painting defect exists on the automobile body 20 to which paint has been applied, the displacement device/actuator 100 is energized, and the machine base 12 is positioned at a predetermined location of the automobile body 20. Thereafter, or prior to such displacement, both the first slit light source 14 and the second slit light source 16 are turned on.

A portion of the light emitted from the first slit light source 14 passes through the translucent portions 26a of the translucent cover 26, and a portion of such light is blocked by the light shielding lines 28. Consequently, the first slit light L1 is formed, and the first slit light L1 is made directly incident on the automobile body 20 in a vertically downward direction.

A portion of the light emitted from the second slit light source 16 passes through the translucent portions 34a of the translucent cover 34, and a portion of such light is blocked by the light shielding lines 36. Consequently, the second slit light L2 is formed. As noted above, the second slit light L2 proceeds in a horizontal direction toward the opposing long side wall, and is made incident on the half mirror 38. The second slit light L2 is refracted by the half mirror 38, whereupon the direction in which the second slit light L2 proceeds changes to a vertical downward direction. The second slit light L2 which is refracted in this manner is made incident on the automobile body 20.

In the foregoing manner, the first slit light L1 from the first slit light source 14 is made incident on a location of the automobile body 20 that faces toward a location where the through hole 30 is not formed, whereas the second slit light L2 from the second slit light source 16 is made incident on a location of the automobile body 20 that faces toward the location where the through hole 30 is formed.

In this case, according to the present embodiment, together with the second slit light source 16 and the half mirror 38 being provided inside the through hole 30, the second slit light source 16 and the half mirror 38 are set with sizes so that the through hole 30 can be closed by both of them. Therefore, the light emitted by the second slit light source 16 is not blocked by the inner walls of the through hole 30. Stated otherwise, the formation of a shadow of the machine base 12 on the automobile body 20 is avoided.

Figure 3:
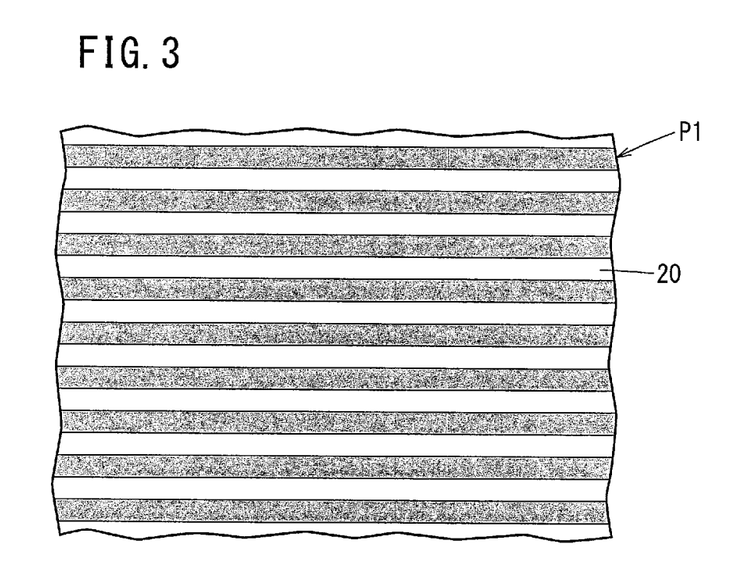
FIG. 3 is a plan view showing a striped shaped light and dark pattern that is formed on an automobile body as an object to be photographed.

Consequently, the stripe shaped light and dark pattern P1 is formed without interruption on the automobile body 20, as shown in FIG. 3.

The camera 40 captures an image of the light and dark pattern P1, and transmits the captured image as image information to the computer (image analysis processing unit). The computer carries out a binarization process with respect to the image information, and on the basis of the results of such an analysis, a determination is made as to whether or not protuberances exist as painting defects. As noted above, since a shadow of the machine base 12 is not formed on the automobile body 20 and the light and dark pattern P1 is formed continuously, the binarization process can be performed with high reliability, or stated otherwise, whether or not protuberances exist on the automobile body 20 can be determined with high accuracy.

The displacement device/actuator 100 displaces the machine base 12 and the camera 40 continuously. Accompanying displacement of the machine base 12, the first slit light source 14 and the second slit light source 16 also are displaced integrally therewith. Consequently, the positions irradiated with the first slit light L1 and the second slit light L2, and the location photographed by the camera 40, or stated otherwise, the inspection location, change continuously. As a result, inspection of defects can be implemented over a wide area of the automobile body 20.

When a protuberance is determined to be present within the light and dark pattern P1, for example, a predetermined marking process is performed with respect to the protuberance. If the number of protuberances is small, the protuberances are removed by grinding or the like. On the other hand, if the number of protuberances is large, it may be preferable to perform repainting of the automobile body 20. In the foregoing manner, an automobile body 20 which is superior in aesthetic appearance can be obtained.

The present invention is not limited in particular to the embodiments discussed above, and various modifications can be made thereto within a range that does not depart from the spirit and gist of the present invention.

Figure 4:
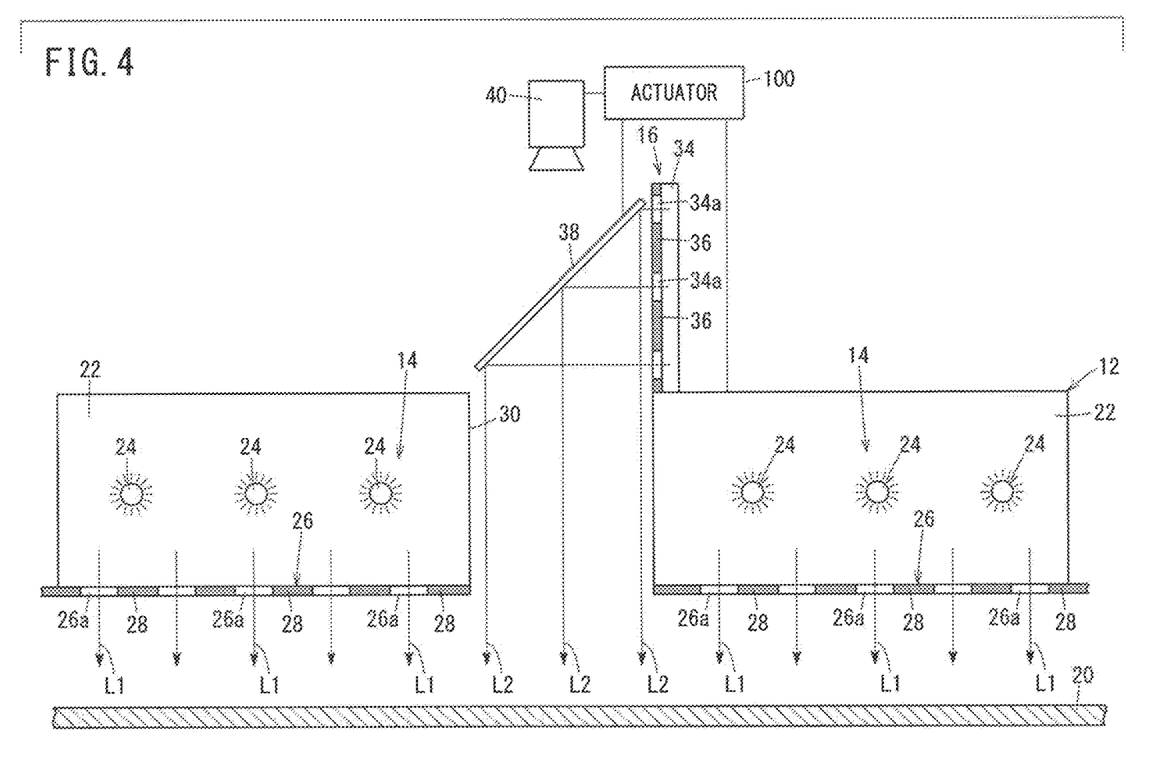
FIG. 4 is a schematic vertical cross-sectional view of principal parts of a defect inspection apparatus in which a half mirror and a second slit light source are disposed above a through hole.

For example, the arrangement locations of the second slit light source 16 and the half mirror 38 are not limited to being in the interior of the through hole 30, and they may be disposed at the positions shown in FIG. 4. For example, the second slit light source 16 is disposed in the vicinity of the upper opening of the through hole 30, and the half mirror 38 is arranged upwardly of the through hole 30. In this case as well, the second slit light L2 from the second slit light source 16 first proceeds in a horizontal direction. Thereafter, the second slit light L2 is refracted by the half mirror 38 and proceeds in a vertical downward direction, whereupon the second slit light L2 is made incident on the automobile body 20. Consequently, the same inspection results are obtained as in the case shown in FIG. 2.

In either of these cases, in the event that a defect inspection is performed with respect to a side surface of the automobile body 20, the first slit light L1 may be made to proceed in a horizontal direction. In this case, the second slit light L2 initially proceeds in a vertical direction, and then is refracted by the half mirror 38 and proceeds in a horizontal direction.

Further, in the present invention, the object to be inspected is not limited in particular to being a paint material, and the invention may be applied to other coating materials. In this case as well, it is possible to determine whether or not defects exist on the basis of whether or not protuberances are present.

Furthermore, a reflecting mirror may be disposed above the half mirror 38, and a location reflected on the reflecting mirror may be photographed by the camera 40.

In addition, it goes without saying that the object to be photographed is not limited to being the automobile body 20.

What is claimed is:

1. A defect inspection method of inspecting whether or not a defect exists on an object to be photographed, by irradiating striped illumination with respect to the object to be photographed, and based on an image obtained from the object to be photographed, comprising the steps of:

directly irradiating first striped illumination on the object to be photographed from a first slit light source disposed in a machine base, together with refracting second striped illumination from a second slit light source by a half mirror, and irradiating the second striped illumination on the object to be photographed through a through hole; and photographing the object to be photographed which is irradiated with the first striped illumination and the second striped illumination by a camera through the half mirror;

wherein the irradiating and the photographing are continuously performed while the machine base, the second slit light source, the half mirror, and the camera are displaced by an actuator.

2. The defect inspection method according to claim 1, wherein:

the second slit light source is disposed in the vicinity of an upper opening of the through hole formed in the machine base, and the second striped illumination proceeds in a direction that intersects with respect to the direction in which the first striped illumination proceeds; and the half mirror is disposed above the through hole, and the second striped illumination is refracted toward the object to be photographed.

3. The defect inspection method according to claim 1, wherein:

the second slit light source is disposed in the through hole that is formed in the machine base, and the second striped illumination proceeds in a direction that intersects with respect to the direction in which the first striped illumination proceeds; and the half mirror is disposed in the through hole, and the second striped illumination is refracted toward the object to be photographed.

4. The defect inspection method according to claim 3, wherein:

the through hole is formed in a rectangular shape, and the second slit light source is installed on a first inner wall of the through hole, and further, the second striped illumination is irradiated in such a manner as to proceed toward a second inner wall that faces toward the first inner wall; and the half mirror is disposed in such a manner as to close the through hole together with the second slit light source, and so that the second striped illumination is refracted by the half mirror.

5. A defect inspection apparatus adapted to inspect whether or not a defect exists on an object to be photographed, by irradiating striped illumination with respect to the object to be photographed, and based on an image obtained from the object to be photographed, comprising:

a machine base in which a through hole is formed, and in which there is provided a first slit light source adapted to directly irradiate first striped illumination on the object to be photographed;

a second slit light source adapted to irradiate second striped illumination on the object to be photographed through the through hole;

a half mirror adapted to refract the second striped illumination in a direction so that the second striped illumination proceeds toward the object to be photographed; and a camera adapted to photograph through the half mirror the object to be photographed which is irradiated with the first striped illumination and the second striped illumination; and an actuator adapted to displace the machine base, the second slit light source, the half mirror, and the camera.

6. The defect inspection apparatus according to claim 5, wherein:

the second slit light source is disposed in the vicinity of an upper opening of the through hole formed in the machine base such that the second striped illumination proceeds in a direction that intersects with respect to the direction in which the first striped illumination proceeds; and the half mirror is disposed above the through hole in such a manner as to refract the second striped illumination toward the object to be photographed.

7. The defect inspection apparatus according to claim 5, wherein:

the second slit light source is disposed in the through hole formed in the machine base such that the second striped illumination proceeds in a direction that intersects with respect to the direction in which the first striped illumination proceeds; and the half mirror is disposed in the through hole.

8. The defect inspection apparatus according to claim 7, wherein:

the through hole is of a rectangular shape, and the second slit light source is installed on a first inner wall of the through hole, and further, the second striped illumination is irradiated in such a manner as to proceed toward a second inner wall that faces toward the first inner wall; and the half mirror closes the through hole together with the second slit light source.

* * * * *